United States Patent
O'Hara et al.

(10) Patent No.: US 6,464,686 B1
(45) Date of Patent: Oct. 15, 2002

(54) POLYURETHANE FEEDING TUBE AND ASSOCIATED ADAPTORS

(75) Inventors: Derek P. O'Hara, Cloongoona; Brendan J. Duggan, Top Road, both of (IE); Gail M. Comer, Libertyville, IL (US); Donald J. Goldhardt, Grove City; Liliana M. Sanmiguel, Powell, both of OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/416,719

(22) Filed: Oct. 13, 1999

Related U.S. Application Data

(63) Continuation-in-part of application No. 09/010,411, filed on Jan. 21, 1998, now Pat. No. 6,093,179.

(51) Int. Cl.$^7$ .................. A61M 25/16; A61M 25/00; A61M 5/00
(52) U.S. Cl. ................ 604/539; 604/284; 604/256
(58) Field of Search .................. 604/93.01, 175, 604/264, 284, 523, 533–539, 167.02, 256; 215/295, 296, 298, 300

(56) References Cited

U.S. PATENT DOCUMENTS

| | | |
|---|---|---|
| 3,995,628 A | 12/1976 | Gula et al. |
| 4,342,313 A | 8/1982 | Chittenden |
| 4,573,576 A | 3/1986 | Krol |
| 4,668,225 A | 5/1987 | Russo et al. |
| 4,713,059 A | 12/1987 | Bickelhaupt et al. |
| 4,778,447 A * | 10/1988 | Velde et al. .................. 604/29 |
| 4,781,704 A | 11/1988 | Potter .......................... 604/270 |
| 5,057,093 A | 10/1991 | Clegg et al. |
| 5,080,650 A | 1/1992 | Hirsch et al. |
| 5,098,378 A | 3/1992 | Piontek et al. |
| 5,139,486 A | 8/1992 | Moss |
| 5,243,679 A | 9/1993 | Sharrow et al. |
| 5,290,250 A | 3/1994 | Bommaritio |
| 5,366,444 A | 11/1994 | Martin |
| 5,391,159 A | 2/1995 | Hirsch et al. |
| 5,399,173 A * | 3/1995 | Parks et al. .................. 604/282 |
| 5,411,491 A | 5/1995 | Goldhardt et al. |
| 5,740,933 A * | 4/1998 | Conti et al. .................. 215/256 |
| 5,840,065 A | 11/1998 | Goldhardt et al. |
| 6,019,746 A * | 2/2000 | Picha et al. .................. 604/175 |

FOREIGN PATENT DOCUMENTS

| | | |
|---|---|---|
| WO | WO 97/11736 | 4/1997 |
| WO | WO 97/47351 | 12/1997 |
| WO | WO 99/37214 | 7/1999 |
| WO | WO 01/26723 | 4/2001 |

* cited by examiner

Primary Examiner—Michael J. Hayes
(74) Attorney, Agent, or Firm—Brian R. Woodworth; Michael R. Crabb

(57) ABSTRACT

A feeding tube assembly includes a feeding tube, a polyurethane feeding tube adaptor having an inlet conduit and an outlet conduit, and a removable cap for selectively closing the inlet conduit. The surface configuration of the cap that causes frictional engagement with the inlet conduit is non-complementary therewith in a common transverse plane and has a cross-sectional shape substantially different than that of the corresponding surface configuration of the inlet conduit. This difference in surface configurations can be established by providing one or both of the surfaces with a series of protuberances, indentations, or other surface variations.

10 Claims, 5 Drawing Sheets

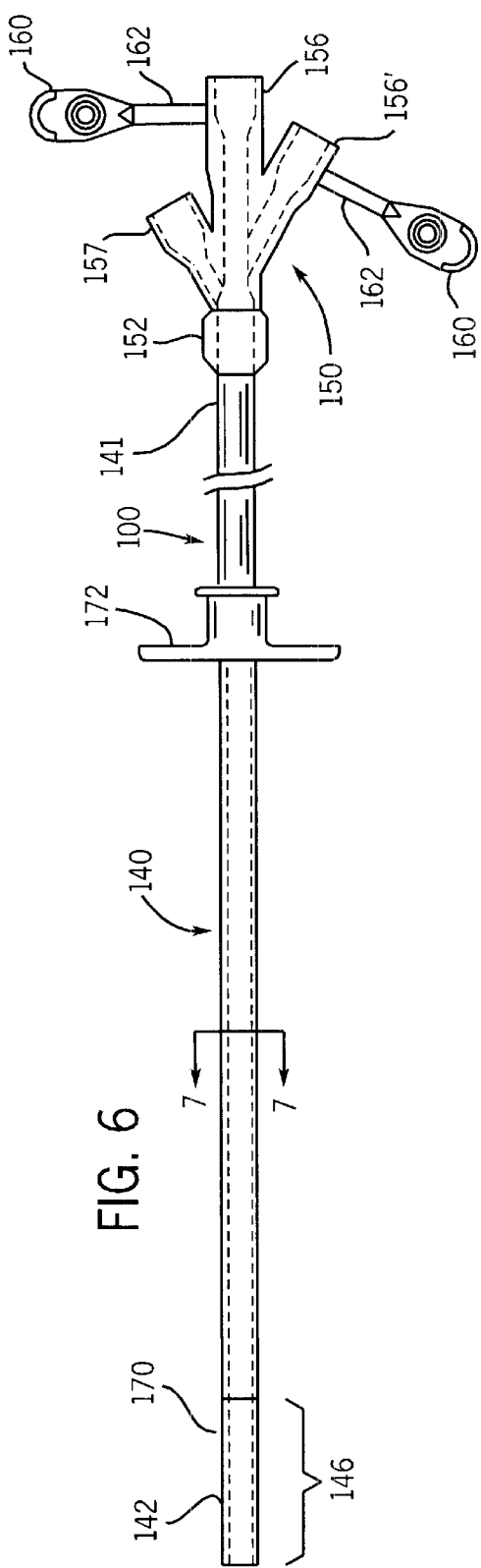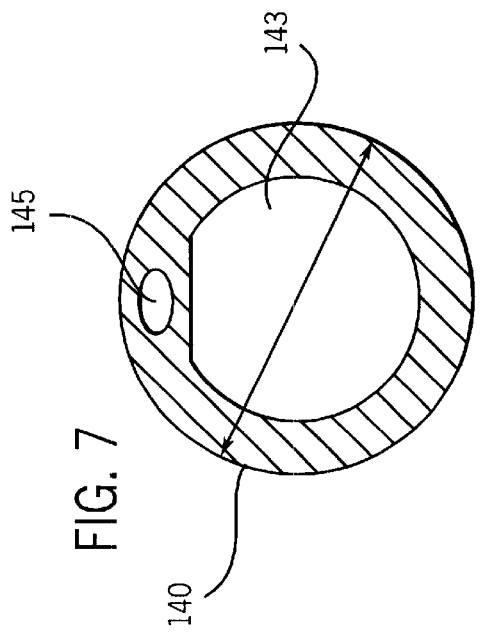

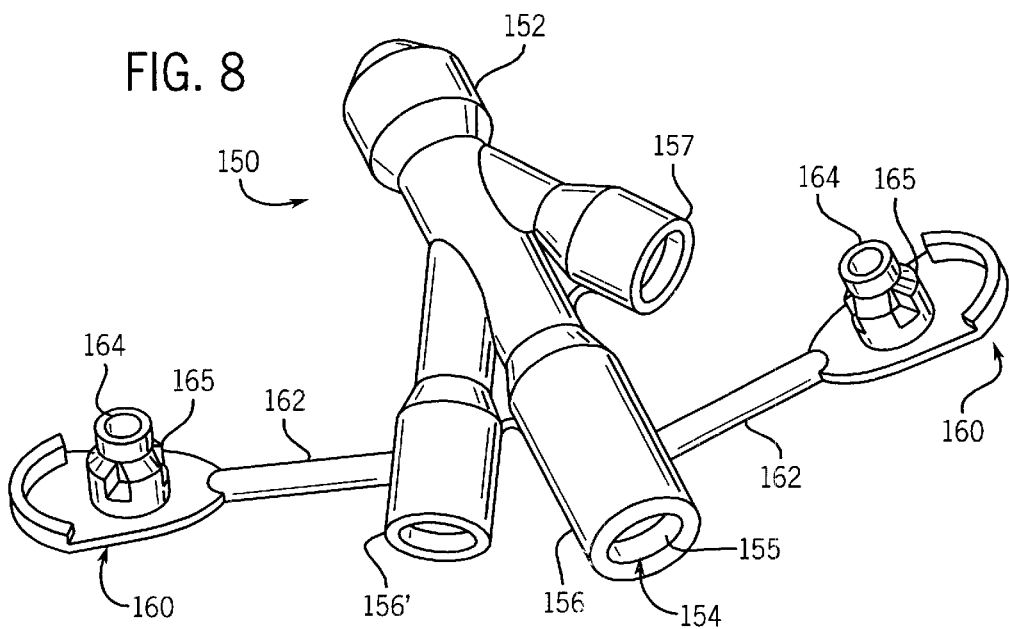
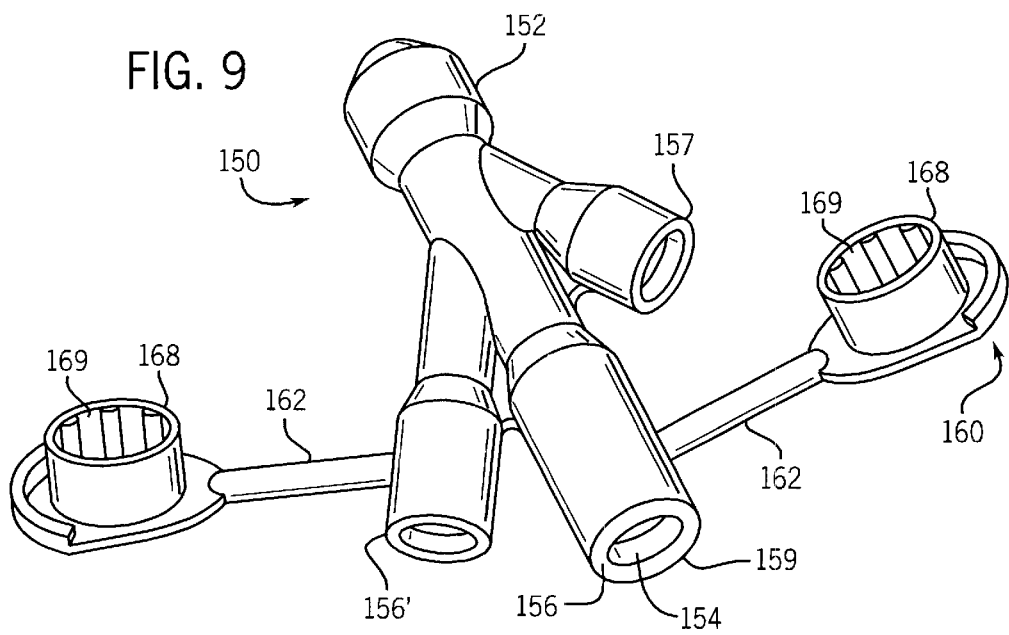

POLYURETHANE FEEDING TUBE AND ASSOCIATED ADAPTORS

This is a continuation-in-part application of prior application Ser. No. 09/010,411, now U.S. Pat. No. 6,093,179 filed Jan. 21, 1998.

BACKGROUND OF THE INVENTION

1. Field of the Invention

This invention relates to an apparatus useful in the placement of a percutaneous endoscopic gastrostomy tube. In particular, the present invention is directed to an introducer attached to a receptacle about which a placement wire is positioned. Following insertion of the introducer into a selected portion of a patient's gastrointestinal tract, the placement wire is inserted into a patient through the introducer by rotating the receptacle, thereby advancing the wire through the introducer.

The present invention also relates to a feeding tube assembly for placement in the gastrointestinal tract a patient. Particularly, the feeding tube assembly includes a feeding tube made of polyurethane, and more preferably Carbothane, and a feeding tube adaptor provided at a first end portion thereof. In accordance with one aspect of this invention, the feeding tube connector is made of a substantially rigid material and includes a retention member for friction engagement with the feeding tube. In accordance with another aspect of the invention, the feeding tube connector is provided with a cap, both of which being made of a polyurethane, wherein the cap has an engagement surface with a surface configuration different than that of a corresponding surface of the feed tube connector.

2. Description of Related Art

Gastrostomy and jejunostomy tubes are used to deliver nutritional products to the gastrointestinal tract of a patient having difficulty ingesting food. Gastrostomy tubes deliver the nutritional products percutaneously from an external source, through the patient's abdominal wall, and directly to the patient's stomach, while jejunostomy tubes deliver the nutritional products percutaneously into the patient's jejunum or small bowel. In addition to primary placement percutaneously through a patient's abdominal wall, gastrostomy and jejunostomy tubes can be placed into the patient's gastrointestinal tract through a mature stoma formed in the abdominal wall, or through the nasal passage using nasogastric or nasojejunal tube, respectively. Gastrostomy, jejunostomy, nasogastric and nasojejunal tubes are referred to collectively herein as "feeding tubes," unless otherwise noted.

The first step for the primary percutaneous placement of a feeding tube in a patient typically involves the passing of an endoscope down the patient's esophagus in order to view the esophagus and determine whether there are any obstructions or lesions in the esophagus that will inhibit or preclude passage of the feeding tube through the esophagus. The endoscope also is used to examine the interior of the stomach and/or the small bowel. Next, the doctor visually selects the site through which the feeding tube will be introduced into the stomach and transilluminates the selected site by directing light outwardly from the endoscope such that the light shines through the patient's abdominal wall, thereby allowing the doctor to identify the entry site from a point outside of the patient's body. The doctor then inserts a catheter or introducer through the patient's abdominal wall and into the stomach at the selected entry site. A first end of a placement wire is then passed through the introducer and into the stomach. The first end of the wire is grasped using a grasping tool associated with the endoscope, and the endoscope and the placement wire are drawn outwardly from the patient's stomach and esophagus through the patient's mouth. Upon completing this step of the procedure, a second end of the wire remains external to the patient's abdominal wall while the first end of the wire extends outwardly from the patient's mouth.

Placement wires can have a variety of forms. In one commercially available embodiment, the placement wire is a doubled wire coated with a biocompatible plastic material. However, other forms of placement wires are well known. These placement wires typically are provided in a sterile package for use by a medical professional. For example, the placement wire can be coiled and placed in a sealed pouch. The wire is removed from the pouch immediately prior to placement in a patient. This packaging methodology presents certain disadvantages in that the wire is prone to entanglement during insertion into the patient. Thus, the wire must be carefully manipulated in order to ensure that it is fed properly through the introducer and into the patient. Such manipulation may result in touch contamination of the wire as it is manipulated. Further, in order to ensure that the wire is properly fed into the patient's stomach, it is sometimes necessary to have one person manipulate the wire while a second person feeds the wire into the patient. This need for additional medical personnel increases the cost of placing the feeding tube in the patient.

In a different commercially available embodiment, the wire is a "silk" type pull thread that is loosely coiled in a provided holder. The thread extends through a hole in the holder and can be pulled outwardly from the holder through the hole. As the endoscope is withdrawn through the patient's esophagus, an assistant must carefully pull the thread out of the holder and allow it to feed through the catheter. This embodiment also presents certain disadvantages due to the fact that an assistant is required in order to manipulate and feed the thread into the catheter. In addition, it typically is necessary to create a knot in the end of the thread before attaching it to a feeding tube. In some cases, creation of this knot can be difficult due to the physical characteristics of the silk thread after it has been drawn through the patient's stomach, esophagus, and mouth.

In another commercially available embodiment, the placement wire is retained in a coil of rigid tubing. The wire can be difficult to manipulate and therefore may require the presence of an assistant to withdraw the wire from the coiled tubing. However, this embodiment does tend to reduce tangling of the placement wire during placement of the wire in the patient. Yet another commercially available embodiment includes a placement wire provided in a circular dispenser. Although this embodiment tends to minimize tangling of the placement wire, the wire still can be difficult to dispense from the circular dispenser and therefore require the presence of an assistant.

It is preferable to provide a placement wire in such a way that (a) the possibility of entanglement of the wire is minimized; (b) the possibility of touch contamination of the wire is minimized; and (c) withdrawal of the wire from its packaging does not require additional personnel. The present invention addresses each of these.

With the wire properly inserted, initial or primary placement of a feeding tube percutaneously into the gastrointestinal tract of the patient can be performed. In one technique for primary feeding tube placement, the first end of the placement wire is attached to a first end of a feeding tube.

Attachment of the feeding tube to the first end of the placement wire is facilitated by a loop on the first end of the placement wire and by a complementary loop on the first end of the feeding tube. By pulling on the second end of the wire positioned external to the patient's abdominal wall, the feeding tube is pulled through the patient's mouth and esophagus, and into stomach. Further pulling of the second end of the wire causes the first end of the feeding tube to exit percutaneously from the stomach through a tract in the abdominal wall formed by the introducer. The feeding tube is pulled outwardly through the tract until a retaining member mounted on the second end of the feeding tube engages the interior of the stomach. This technique is referred to as a "pull" technique.

In an alternative technique for primary feeding tube placement, a channel defined through the feeding tube is positioned over the wire such that the feeding tube can be pushed along the length of the wire. As the feeding tube is pushed over the wire, it passes through the patient's mouth, esophagus, and stomach until the first end of the feeding tube exits through the incision in the abdominal wall. The feeding tube is then drawn outwardly through the abdominal tract until a retaining member on the internal or second end of the feeding tube engages the interior of the stomach. The wire is then withdrawn from the patient through the feeding tube channel. This technique is referred to as a "push" technique.

Yet another method may be used for percutaneous placement of the feeding tube, particularly when passage through the esophagus is precluded. This method, which is commonly known as the "poke" technique, is most often used for placement of a feeding tube having a balloon-type internal retaining member. Once a safe site into the stomach is identified, the poke technique requires that the stomach wall be retracted and secured against the abdominal wall of the patient using a known anchoring device, such as T-Fastenerst®. One or more dilators are then used in sequence to form an adequate tract of sufficient size through which the feeding tube and the retaining member, in a deflated state, can be inserted. The retaining member is then inflated in its proper position to secure the placement of the feeding tube.

After a stoma tract has fully formed through the abdominal wall of the patient using any of the techniques summarized above, the initial feeding tube can be removed if secondary placement of a different feeding tube is desired or necessary. In this manner, a new feeding tube can be inserted directly into the mature stoma tract that is formed through the patient's abdominal wall and retained in a conventional manner.

A variety of feeding tube configurations made of different materials are well known, and are each suitable for its intended purpose. There remains a continued need, however, for feeding tube assemblies of enhanced operational characteristics and cost effective construction.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, the invention includes a method for placing a feeding tube placement wire in a patient. The method includes the step of providing a placement wire dispenser. The dispenser includes a rotatable placement wire receptacle that defines a placement wire outlet. The dispenser further includes a tube extending outwardly from the placement wire receptacle. The tube defines a placement wire inlet that is in communication with the placement wire outlet of the receptacle. A placement wire is wound about the receptacle, and is in mechanical engagement with the receptacle, such that rotation of the placement wire receptacle causes a first end of the placement wire to be advanced through the placement wire outlet, through the placement wire inlet of the tube, and through the tube. A first end of the tube is constructed for insertion through a patient's abdominal wall and into a patient's stomach. The method further includes the step of placing the first end of the tube through a patient's abdominal wall and into a patient's stomach. Rotational movement is imparted to the receptacle so as to advance the placement wire through the placement wire outlet, through the placement wire inlet, through the tube, and into a patient's stomach.

The present invention also includes a placement wire dispenser. The dispenser includes a rotatable placement wire receptacle that defines a placement wire outlet. The dispenser further includes a tube extending outwardly from the placement wire receptacle. The tube defines a placement wire inlet that is in communication with the placement wire outlet of the receptacle. A placement wire is wound about the receptacle, and is in mechanical engagement with the receptacle, such that rotation of the placement wire receptacle causes a first end of the placement wire to be advanced through the placement wire outlet, through the placement wire inlet of the tube, and through the tube. A first end of the tube is constructed for insertion through a patient's abdominal wall and into a patient's stomach.

The present invention further is directed to a feeding tube placement kit. The kit includes a placement wire dispenser. The dispenser includes a rotatable placement wire receptacle that defines a placement wire outlet. The dispenser further includes a tube extending outwardly from the placement wire receptacle. The tube defines a placement wire inlet that is in communication with the placement wire outlet of the receptacle. A placement wire is wound about the receptacle, and is in mechanical engagement with the receptacle, such that rotation of the placement wire receptacle causes a first end of the placement wire to be advanced through the placement wire outlet, through the placement wire inlet of the tube, and through the tube. A first end of the tube is constructed for insertion through a patient's abdominal wall and into a patient's stomach. The kit further includes a feeding tube having a first end portion and a second end portion. The feeding tube defines a feeding lumen therethrough. A retaining member is disposed on the second end portion of the feeding tube.

The present invention also is directed to a feeding tube adaptor having an outlet conduit and an inlet conduit. An exterior surface of the outlet conduit is configured such that it has a first section having an increasing circumferential dimension from an outlet end of the adaptor to an inlet end of the adaptor. The exterior surface of the outlet conduit further is configured such that it has a second section having a decreasing circumferential dimension from an outlet end of the adaptor to an inlet end of the adaptor. The first and second sections of the exterior surface of the outlet conduit define a tube retention member, and preferably are positioned adjacent each other.

Additionally, the present invention is directed to a feeding tube assembly including a feeding tube made of a polyurethane, preferably Carbothane. The feeding tube has a first end portion, a second end portion and at least one lumen defined therein. The feeding tube assembly further includes a feeding tube adaptor having an inlet conduit and an outlet conduit, preferably made of a substantially rigid material, wherein the outlet conduit has an outlet end to be inserted into a lumen at the first end portion of the feeding tube for fluid communication therebetween. The exterior surface of the outlet conduit defines a retention member to engage an interior surface at the first end portion of the feeding tube when the outlet end of the outlet conduit is inserted within the lumen of the feeding tube. The retention member includes a first section having an exterior peripheral dimension increasing with increasing distance from the outlet end of the outlet conduit, and a second section having an exterior peripheral dimension decreasing with increasing distance from the outlet end of the outlet conduit.

In accordance with another aspect, the present invention is directed to a feeding tube assembly including a feeding tube, a feeding tube adaptor having a first inlet conduit, and a removable cap made of polyurethane to close selectively an inlet port of the first inlet conduit. The cap has an engagement surface to engage a corresponding surface of the first inlet conduit, wherein the engagement surface of the cap has a surface configuration different than that of the corresponding surface of the first inlet conduit. For example, the inlet conduit can include a port defined by an interior surface and the cap can include a plug to be inserted into the port, wherein the engaging surface of the cap is an exterior surface of the plug and the corresponding surface of the inlet conduit is an interior surface of the inlet conduit. Alternatively, the cap can include a peripheral flange, such that the engaging surface of the cap is an interior surface of the peripheral flange that engages a corresponding surface of the exterior surface of the inlet conduit. The difference in surface configurations can be established by providing one or both of the surfaces with a series of protuberances, a series of indentations, a different cross-sectional shape, or a combination thereof.

It is to be understood that both the foregoing general description and the following detailed description are exemplary and are intended to provide further explanation of the invention claimed.

The accompanying drawing, which is incorporated in and constitutes part of this specification, is included to illustrate and provide a further understanding of the method and system of the invention. Together with the description, the drawing serves to explain the principles of the invention.

BRIEF DESCRIPTION OF THE DRAWINGS

In the accompanying drawings that form part of the specification, and in which like numerals are employed to designate like parts throughout the same:

FIG. 6 is a plan view of a feeding tube assembly in accordance with an additional aspect of the invention;

FIG. 7 is a cross-sectional view of the feeding tube assembly of FIG. 6, taken along line 7—7;

FIG. 8 is an enlarged perspective view of the feeding tube adaptor of the feeding tube assembly of FIG. 6;

FIG. 9 is an enlarged perspective view of an alternative embodiment of the feeding tube adaptor of the feeding tube assembly of FIG. 6.

DETAILED DESCRIPTION

Reference will now be made in detail to the present preferred embodiments of the invention, an example of which is illustrated in the accompanying drawings. The method and corresponding steps of the invention will be described in conjunction with the detailed description of the system.

While this invention is susceptible of embodiment in many different forms, this specification and the accompanying drawings disclose specific embodiments as examples of the invention. The invention is not intended to be limited to the embodiments so described or shown. The scope of the invention is pointed out in and defined by the appended claims.

The figures illustrating the apparatus show some elements that are known and that will be recognized by one skilled in the art. The detailed descriptions of such elements are not necessary to an understanding of the invention, and accordingly, are herein presented only to the degree necessary to facilitate an understanding of the novel features of the present invention.

The present invention is practiced with certain conventional components the details of which, although not fully illustrated or described, will be apparent to those having skill in the art and an understanding of the necessary functions of such components.

A method of the invention will be described herein in the context of the accompanying figures which depict a method for placing a feeding tube percutaneously into the stomach of a patient. However, it will be appreciated by one of ordinary skill in the art that this method of the present invention can be employed for the purposes of placing feeding tubes into other preselected sections of the gastrointestinal tract of a patient, e.g., the small bowel. Accordingly, the detailed description set forth herein is intended to cover methods for placing feeding tubes into any preselected section of the gastrointestinal tract of a patient, including, but not limited to, the stomach and the small bowel.

Figure 1:
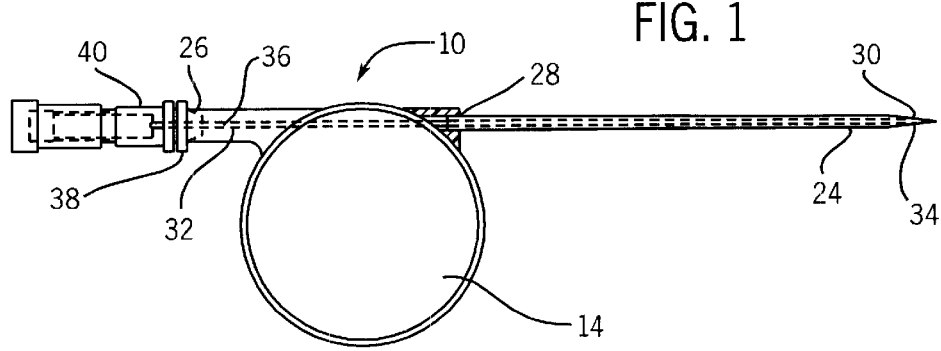
FIG. 1 is a perspective view of a placement wire dispenser constructed in accordance with the present invention.
Figure 2:
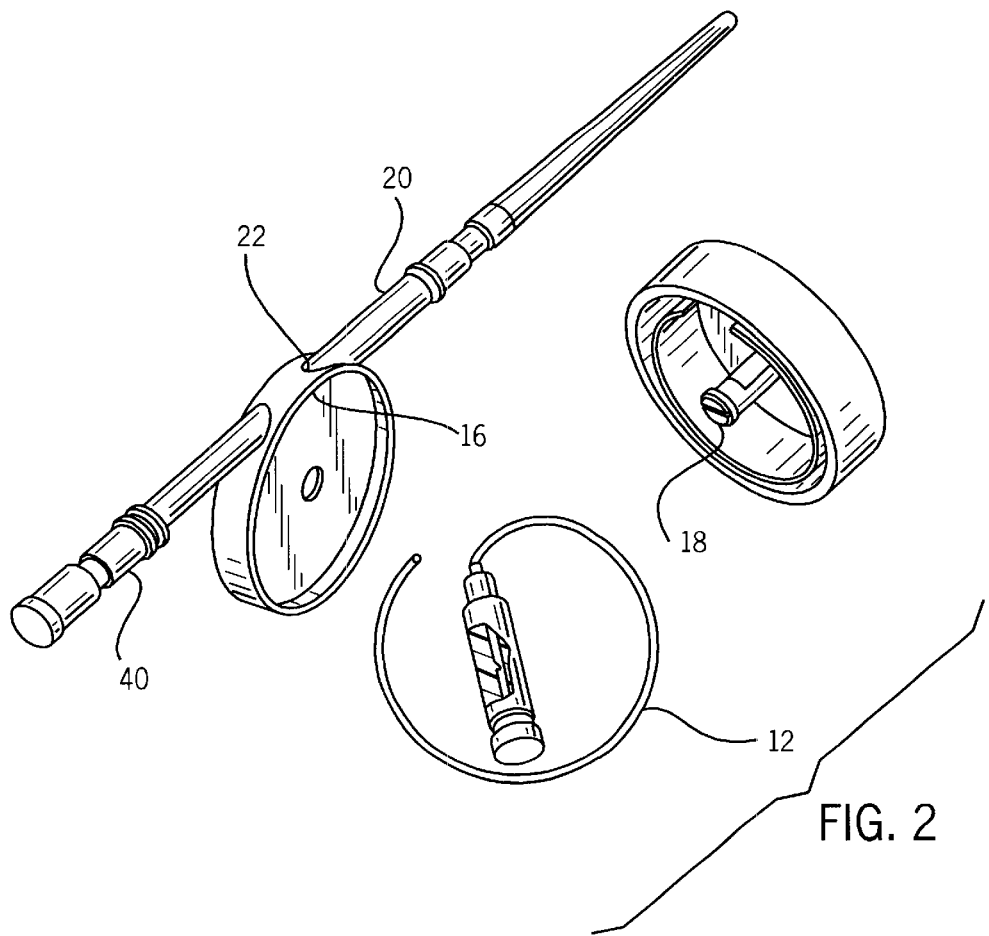
FIG. 2 is an exploded view of a placement wire dispenser constructed in accordance with the present invention.
Figure 3:
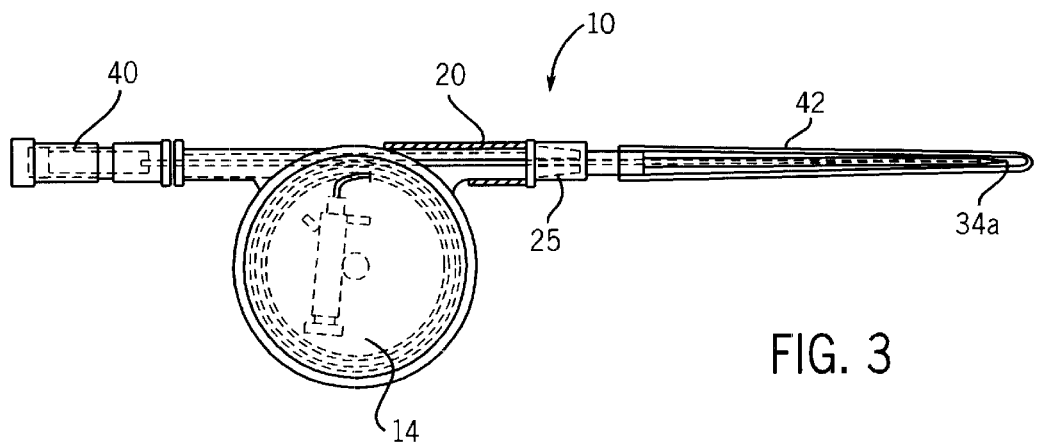
FIG. 3 is a second perspective view of a placement wire dispenser constructed in accordance with the present invention.
Figure 4:
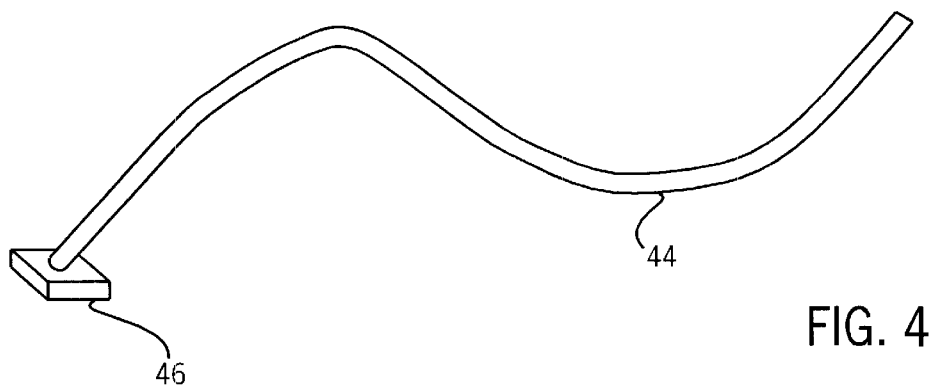
FIG. 4 is a perspective view of a feeding tube constructed in accordance with the present invention.

Dispenser 10 constructed in accordance with the present invention is generally depicted in FIG. 1. Dispenser 10 is constructed substantially in accordance with the teachings set forth in U.S. Pat. No. 4,342,313 which is incorporated herein by reference. U.S. Pat. No. 4,342,313 is assigned of record to Abbott Laboratories, the assignee of the invention disclosed and claimed herein. Applicants also hereby incorporate herein by reference the teachings of U.S. Ser. No. 08/733,900 filed Oct. 18, 1996, now U.S. Pat. No. 5,810,835 which was a continuation of U.S. Ser. No. 08/365,398 filed Dec. 28, 1994, now abandonded.These applications also are assigned of record to Abbott Laboratories.

Dispenser 10 includes a placement wire 12 wound about a receptacle 14. Placement wire 12 can be constructed of a variety of known, biocompatible materials and can have a variety of known configurations useful in the placement of percutaneous endoscopic gastrostomy and jejunostomy tubes. In a preferred embodiment, wire 12 includes a pair of wires coated with a biocompatible, plastic material. Receptacle 14 preferably contains placement wire 12 therein such that placement wire 12 is not exposed to an external environment of receptacle 14 until it is dispensed therefrom, as described in detail herein. Receptacle 14 defines wire outlet 16 therethrough. Wire outlet 16 is configured such that placement wire 12 can be passed therethrough, as explained in detail herein.

Placement wire 12 is in mechanical engagement with receptacle 14 such that rotation of receptacle 14 causes placement wire 12 to rotate and advance outwardly from receptacle 14. One of ordinary skill in the art will appreciate that a variety of methods can be used to mechanically engage placement wire 12 with receptacle 14 such that rotation of receptacle 14 will cause wire 12 to be dispensed therefrom. The present invention is intended to encompass all such methodologies. A spindle or handle 18 can be mechanically connected to receptacle 14 in order to facilitate manual rotation of receptacle 14.

A tubular portion 20 is mounted on receptacle 14 as depicted in FIG. 1. Tubular portion 20 defines wire inlet 22 therethrough. Wire inlet 22 is configured such that placement wire 12 can be passed therethrough. Wire inlet 22 and wire outlet 16 are disposed such that they are in communication with one another, i.e., such that placement wire 12 will pass through wire outlet 16, through wire inlet 22, and into tubular portion 20 when receptacle 14 is rotated. Tubular portion 20 has a first end portion 24 and a second end portion 26. In the embodiment of the present invention depicted in FIG. 1, both first end portion 24 and second end portion 26 are open such that channel 28 defined by tubular portion 20 is open to an external environment of tubular portion 20 at first end portion 24 and second end portion 26. However, it will be appreciated that second end portion 26 can be closed such that channel 28 is not open to an external environment of tubular portion 20 without departing from the spirit of the present invention. This will be explained in greater detail below.

First end portion 24 of tubular portion 20 can be constructed such that it has a substantially flat terminal end 30, as depicted in FIG. 1. In the embodiment depicted in FIG. 1, piercing member 32 is provided and is constructed such that it can be inserted through channel 28 of tubular portion 20 from second end portion 26 to first end portion 24. It will be appreciated that second end portion 26 of tubular portion 20 must be open to an external environment of tubular portion 20 in this embodiment of the present invention in order to permit piercing member 32 to be inserted therein. Piercing member 32 is constructed such that piercing tip 34 thereof is disposed outwardly from terminal end 30 when piercing member 32 is properly positioned within tubular portion 20. Piercing member 32 can be solid. However, in the embodiment of the present invention depicted in the accompanying figures, piercing member 32 defines channel 36 therethrough. Piercing member 36 has a hub end 38 opposite piercing tip 34. Hub member 40 is mounted on hub end 38. Hub member 40 is configured such that selected instruments can be attached thereto. For example, hub member 40 can be constructed such that it can be fluidly connected to a source of pressurized air and such that pressurized air can be directed through channel 36 after piercing tip 34 has been positioned in a patient's stomach, thereby facilitating insuflation of a patient's stomach. Hub member 40 can be configured such that it provides a variety of known connections, including, but not limited to, threading connections, luer connections, and locking luer connections.

It will be appreciated that piercing member 32 can be omitted from the present invention in certain embodiments. For example, first end portion 24 of tubular portion 20 can be constructed such that it can be inserted directly through a patient's abdominal wall and into a patient's stomach, thereby obviating the need for piercing member 32. That is, a piercing tip 34a can be provided on first end portion 24 of tubular portion 20 where the piercing tip is constructed such that it will penetrate through a patient's abdominal wall and into a patient's stomach. In another alternative embodiment, first end portion 24 is substantially flat, as depicted in the accompanying figures. It will be appreciated that first end portion 24 of tubular portion 20 can be inserted through a dilator, an introducer, or a catheter of known constructed that has been inserted through a patient's abdominal wall and into a patient's stomach. In this way terminal end 30 of tubular portion 20 can be positioned in a patient's stomach without the use of piercing member 32 and without the presence of a piercing tip on tubular portion 20. It is to be appreciated that in some cases it may be possible to insert first end portion 24 of tubular portion 20 through a patient's abdominal wall and into a patient's stomach without the use of a piercing member, a piercing tip, a dilator, an introducer, and/or a catheter. If piercing member 32 is not used, it is not necessary for second end portion 26 of tubular portion 20 to provide communication between channel 28 and an external environment of tubular portion 20.

If piercing member 32 is used, or if first end portion 24 of tubular portion 20 includes piercing tip 34a, protective sheath 42 can be provided in order to prevent piercing tip 34, 34a from inadvertently piercing the skin of a medical professional and/or a patient. In the embodiment depicted in the accompanying figures, sheath 42 is a substantially tubular member configured to surround piercing tip 34, 34a. However, it will be appreciated that sheath 42 can have a variety of known configurations without departing from the scope of the present invention.

In a preferred embodiment of the present invention, a one way fluid flow valve 25 is disposed in channel 28 of tubular portion 20 One way fluid flow valve 25 is constructed to impede the flow of fluid, e.g., air, outwardly from the patient through tubular portion 20. One way fluid flow valve 25 is configured such that it permits the movement of placement wire 12 therethrough as wire 12 is advanced from receptacle 14 through tubular portion 20 and into a patient. One way fluid flow valve 25 can have a variety of known configurations without departing from the scope of the present invention set forth in the appended claims. In one embodiment of the present invention, one way fluid flow valve 25 is a duckbilled valve of known construction.

Placement of a feeding tube is facilitated through the use of dispenser 10 of the present invention. In use, dispenser 10 as described herein is provided. A medical professional urges first end portion 24 of tubular portion 20 inwardly through a patient's abdominal wall and into a patient's stomach. In one embodiment of the method of the present invention, first end portion 24 does not include piercing tip 34a and piercing member 32 is not used. In this embodiment, first end portion 24 of tubular portion 20 is inserted through a patient's abdominal wall and into a patient's stomach with or without the use of a dilator, introducer, or catheter, subject to the discretion of the medical professional. In a second embodiment, first end portion 24 has piercing tip 34a associated therewith. In a third embodiment, piercing member 32 is provided and is inserted through channel 28 such that piercing tip 34 is extends outwardly from terminal end 30 of tubular portion 30. In each case, first end portion 24 is urged through the patient's abdominal wall and into the patient's stomach.

If desired, the medical professional can insufflate the patient's stomach by directing pressurized air through channel 28 and into a patient's stomach. If piercing member 32 is used, the pressurized air can be directed through channel 36 of piercing member 32 and into the patient's stomach. In particular, the source of pressurized air can be connected to hub member 40 of piercing member 32. If piercing member 32 is not used, and if second end portion 26 of tubular portion 20 provides open communication between channel 28 and an external environment of tubular portion 20, pressurized air can be directed through second end portion 26 of tubular portion 20 and into the patient's stomach through channel 28 of tubular portion 20.

If piercing member 32 is used, it is then withdrawn from channel 28 by pulling on hub end portion 38 thereof until piercing tip 34 is withdrawn from second end portion 26 of tubular portion 20.

Rotational movement is then imparted to receptacle 14 such that placement wire 12 advances through wire outlet 16, through wire inlet 22, through channel 28, and into the patient's stomach. Rotational movement can be imparted manually or through the use of a mechanical means, e.g., an electrical motor.

After placement wire 12 has been positioned in the patient's stomach, it is grasped using a grasping tool and withdrawn through the patient's esophagus and mouth in accordance with known methodologies. First end portion 24 of tubular portion 20 can then be withdrawn from the patient's stomach. A feeding tube 44 of known construction may be connected to placement wire 12, and the placement wire 12 and the feeding tube 44 are urged through the patient's esophagus and stomach until the feeding tube 44 passes percutaneously through the patient's abdominal wall. In a preferred embodiment, the feeding tube 44 is constructed of a polyurethane material; particularly, Carbothane. Feeding tube 44 can include a known radiopaque material that enables it to be visualized via X-ray or other imaging systems.

A retaining member 46 is mounted on a second end portion of feeding tube 44. Retaining member 46 is constructed to prevent the second end portion of feeding tube 44 from passing through the patient's abdominal wall. Retaining member 46 can have a variety of known configurations and can be constructed of a variety of known materials, including, but not limited to, silicone and polyurethane. For example, but not by limitation, flexible element-type retaining member configurations are disclosed by U.S. Pat. Nos. 5,080,650 and 5,391,159, each of which is incorporated in its entirety by reference herewith.

It has been found that, under certain adverse conditions, these flexible element-type retaining members inadvertently can become detached from feeding tube 44 when feeding tube 44 is constructed of a polyurethane material. This potential problem has been found to be particularly present when feeding tube 44 is constructed of a polyurethane material and retaining member 46 is constructed of a silicone material. This potential problem can be obviated by slip molding retaining member 46 on feeding tube 44. Techniques for slip molding are well known in the art and will not be described herein in detail.

Alternatively, it may be desirable to provide a balloon-type retaining member configuration. Examples of various balloon-type retaining member configurations are disclosed by U.S. Pat. Nos. 5,098,378 and 5,840,065, which are also incorporated in entirety by reference herein. It is noted that these balloon-type retaining members generally are configured for use with a multi-lumen feeding tube, wherein at least one lumen is used for inflation and deflation selectively of the retaining member in a known manner. One such multi-lumen feeding tube is depicted in the representative embodiment of FIG. 7, as will be described in detail below.

Upon proper primary placement of feeding tube 44 through the patient's abdominal wall, a first end portion of feeding tube 44 can be cut to an appropriate length. An external retaining disc 48 can be placed over the first end portion of the feeding tube 44 in order to prevent undesired inward movement of feeding tube 44 through the patient's abdominal wall. The external retaining disc 48 can have a variety of known configurations.

An adaptor 50 can be provided in order to interconnect feeding tube 44 and another in-line feeding element, e.g., a tube extending from a source of enteral nutritional product. In one embodiment, adaptor 50 includes outlet conduit 52 having an exterior surface 54. Adaptor 48 further includes one or more inlet conduits 56. An example of a suitable adaptor 50 is disclosed in U.S. Pat. No. 5,057,093 which is incorporated herein by reference.

Figure 5:
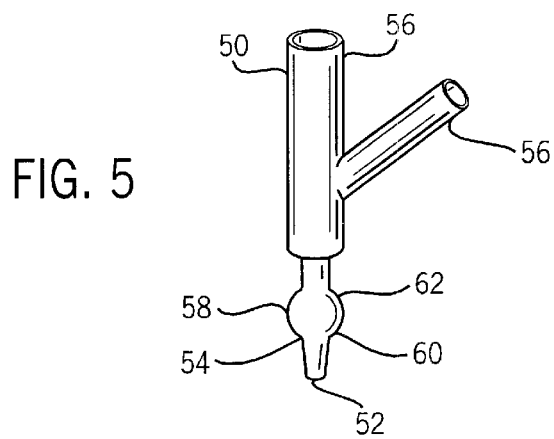
FIG. 5 is a perspective view of an adaptor constructed in accordance with the present invention.

In the event that feeding tube 44 is constructed of a polyurethane material, and in accordance with another aspect of the present invention, it is preferable that exterior surface 54 of outlet conduit 52 define a retention member 58 thereon which prevents feeding tube 44 from slipping off of exterior surface 54 during use. In a preferred embodiment, retention member 58 includes a first section 60 on exterior surface 54. First section 60 has an increasing circumferential dimension viewed from outlet conduit 52 to inlet conduits 56 as shown in FIG. 5. Retention member 58 further includes a second section 62. Second section 62 has a decreasing circumferential dimension viewed from outlet conduit 52 to inlet conduits 56. First section 60 and second section 62 can be positioned adjacent to one another as depicted in the accompanying figures, or can be spaced from one another by an intermediate section having a variety of configurations, e.g., a surface of substantially constant circumferential dimension, without departing from the spirit of the present invention. Preferably, the feeding tube adaptor of this embodiment, or at least the retention member, is made of an acrylonitrile-butadien-styrene (ABS) resin or similar rigid material, such as nylon.

In another aspect of the present invention, a kit for the placement of a feeding tube is provided. The kit includes dispenser 10 and feeding tube 44 constructed in accordance with the above-discussed embodiments thereof. The kit may further include adaptor 50 constructed in accordance with the above-discussed embodiments.

Once a stoma tract has fully formed or matured through the abdominal wall of the patient, the feeding tube can be removed for secondary placement of a different feeding tube if necessary or desired. That is, a new feeding tube assembly can be inserted through the mature stoma tract in a conventional manner without the need for a placement wire or placement wire dispenser. A variety of feeding tube assemblies capable of secondary placement are known and widely available. FIG. 6, however, shows a representative embodiment of a feeding tube assembly, designated generally by reference character 100, in accordance with an additional aspect of the present invention.

The feeding tube assembly 100 includes a feeding tube 140 having a first end portion 141 and a second end portion 142 opposite the first end portion 141. At least one lumen 143 is defined within the feeding tube 140, and extends between the first end portion 141 and the second end portion 142 thereof. The axial length and cross-sectional dimensions of the feeding tube 140 are appropriate for its intended purpose. For example, a feeding tube 140 intended for adult use will have overall dimensions greater than those of a feeding tube 140 intended for pediatric use. The feeding tube 140 may be constructed of any of a variety of known biocompatible materials. Tests indicate, however, that the use of a polyurethane known as Carbothane PC (3575A-B20), which is available from Thermedics, or an equivalent material thereof, provides superior performance and durability.

The feeding tube assembly 100 embodied herein further includes a feeding tube adaptor 150 made of polyurethane mounted at the first end portion 141 of the feeding tube 140. The feeding tube adaptor 150 includes at least a first inlet conduit 156 having an inlet port 154, and an outlet conduit 152 in fluid communication with the first inlet conduit 156. Additional inlet conduits 156' may be provided, as desired or necessary, to allow the secondary introduction of beneficial agents or similar additives into the feeding lumen 143 of the of the feeding tube 140. Furthermore, one or more additional inlet conduits 157 may be provided to accommodate operation of a balloon-type retaining member, if provided, as described further below.

The outlet conduit 152 is connected in fluid communication with the first end portion 141 of the feeding tube 140. This connection between the adaptor and the feeding tube can be accomplished by a variety of known construction techniques. For example, insert molding is preferred to establish a relatively permanent connection, particularly when a multi lumen feeding tube is used, such as previously described in conjunction with a balloon-type retaining member. Alternatively, the feeding tube adaptor 150 can be provided with an insert member (not shown) at the outlet conduit 152, wherein the insert member is made of an acrylonitrile-butadien-styrene (ABS) resin or the like and has an external surface configuration similar to that of the outlet conduit 152 shown in FIG. 5. As such, a polyurethane feeding tube adaptor 150 can be connected to a polyurethane feeding tube 140 in a manner similar to that previously described with regard to the feeding tube adaptor 150 of FIG. 5.

A removable cap 160 also is provided to close selectively each inlet port 154 of the first inlet conduit 156. In this manner, the feeding tube 140, and thus direct access to the gastrointestinal tract, can be sealed from the outside environment when not in use. The cap 160 therefore has an engagement surface to engage a corresponding surface of the first inlet conduit 156 when the cap 160 is positioned to seal the inlet port 154. To prevent misplacement of the cap 160, it is preferred that the cap 160 be permanently connected to the feeding tube adaptor 150, such as by a tether member 162 or similar connector element. Although a separate element may be provided for such connection, it is preferred that the cap 160 be formed integrally with at least a portion of the feeding tube adaptor 150 to reduce the cost of construction.

As noted, the feeding tube adaptor 150 is made of a polyurethane for its performance characteristics. In the preferred embodiment, a polyurethane known as Tecoflex (EG80A-B20) available from Thermedics, or an equivalent material thereof, is used for construction of the feeding tube adaptor 150. If the cap 160 is formed integrally with the feeding tube adaptor 150, as preferred, the cap 160 likewise will be formed of the same or a compatible material of construction for the feeding tube adaptor 150. Such polyurethane materials are susceptible to hydrogen bonding and similar self adhesion phenomenon. As such, and in accordance with an additional aspect of the present invention, the engagement surface of the cap 160 is provided with a surface configuration different than that of the corresponding surface of the first inlet conduit 156.

For example, and as shown in FIG. 8, the inlet port 154 of the inlet conduit 156 is defined by an interior surface 155 and the cap 160 includes a plug 164 to be inserted into the inlet port 154, the engaging surface of the cap 160 therefore is defined, at least in part, by the an exterior surface 165 of the plug 164 and the corresponding surface is defined at least in part by the interior surface 155 of the inlet conduit 156. Alternatively or additionally, and as shown in FIG. 9, the cap 160 may be provided with a peripheral flange 168, such that the engaging surface of the cap 160 is defined by an interior surface 169 of the peripheral flange 168 and the corresponding surface of the inlet conduit 156 is defined by an exterior surface 159 thereof.

Figure 8A:
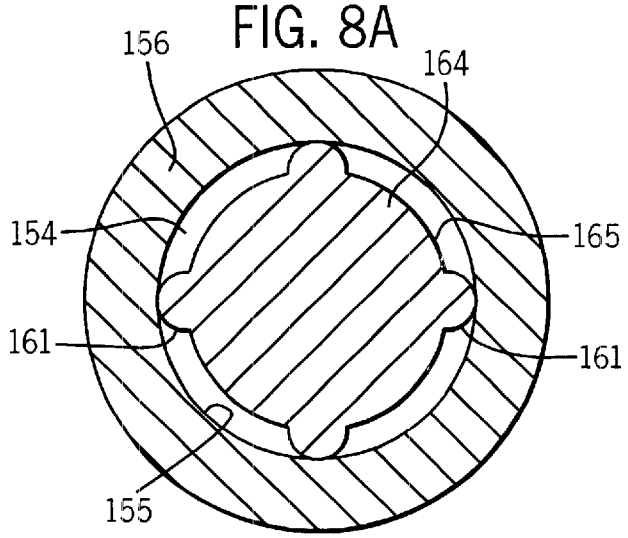
FIG. 8A is an enlarged cross-sectional view depicting one possible surface configuration between the engagement surface of the cap and the corresponding surface of the inlet conduit of the feeding tube adaptor of FIG. 8.
Figure 8B:
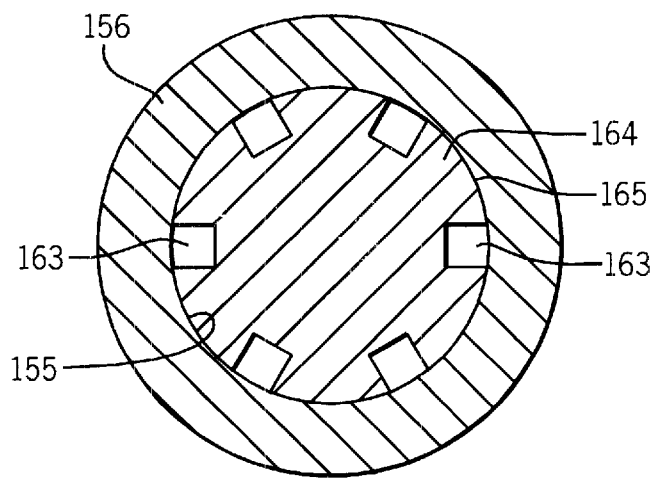
FIG. 8B is an enlarged cross-sectional view depicting another possible surface configuration between the engagement surface of the cap and the corresponding surface of the inlet conduit of the feeding tube adaptor of FIG. 8.
Figure 8C:
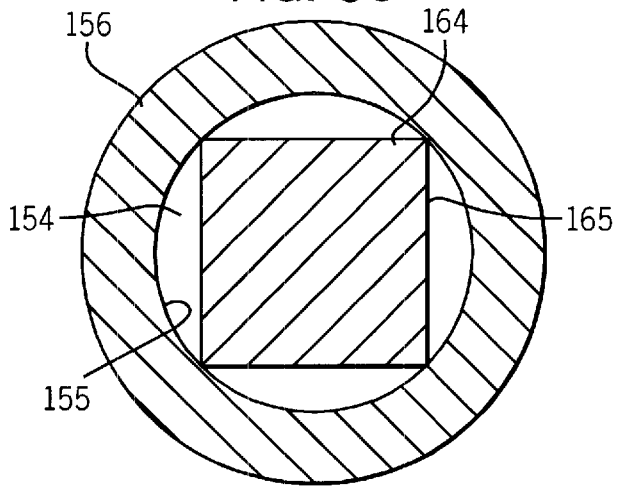
FIG. 8C is an enlarged cross-sectional view depicting an additional surface configuration between the engagement surface of the cap and the corresponding surface of the inlet conduit of the feeding tube adaptor of FIG. 8.

FIGS. 8A through 8C show three possible surface configurations between the engagement surface of the cap and the corresponding surface of an inlet conduit of the feeding tube adaptor of FIG. 8. Each of these three views is taken in cross-section looking into the inlet port 154 toward the outlet conduit 152, with the cap 160 positioned against the end of the inlet conduit 156 opposite the outlet conduit 152 to seal the inlet port 154.

Particularly, FIG. 8A shows that at least one of either the engagement surface or the corresponding surface is provided with a series, i.e., one or more, of protuberances 161 to define a different surface configuration therebetween. Although FIG. 8A shows the protuberances 161 on the plug 164 of the cap 160, such protuberances 161 likewise can be provided on the corresponding surface of the first inlet conduit 156. The protuberances 161 may be provided in any of a variety of forms, including buttons, ribs, ridges, rings, etc. Similarly, the difference in surface configurations between the engagement surface and the corresponding surface can be defined by a series of indents 163 provided in at least one of the two surfaces as shown by the exemplary embodiment of FIG. 8B. Furthermore, the difference in surface configurations between the engagement surface and the corresponding surface can be defined by providing one of the two surfaces with a cross-sectional shape that is different than that of the other surface. For example, but not by limitation, FIG. 8C shows that the inlet port 154 of the inlet conduit 156 can be defined by a circular cross-section, while the cap 160 can be provided with a plug 164 having a generally square or rectangular cross-section sized such that only the corners of the plug 164 engage the interior surface 155 of the inlet port 154.

The feeding tube assembly 100 in accordance with this embodiment of the invention, as thus described, can be used not only for gastrostomy and jejunostomy applications, but also for nasoenteric applications. That is, and provided that the feeding tube 140 has a suitable length and cross-dimension, the feeding tube assembly 100 as thus described can be inserted via the nasal passage into the gastrointestinal tract of a patient in a known manner.

In accordance with an additional aspect of the invention, however, the feeding tube assembly 100 also can be provided with a retaining member 146 attached to the second end portion 142 of the feeding tube 140 when intended for gastrostomy and jejunostomy applications. Any of a variety of known retaining members can be used, including flexible element-type retaining members as previously described. In a preferred embodiment, a balloon-type retaining member 146 is attached to the second end portion 142 of the feeding tube 140. Although the balloon-type retaining member can be constructed and attached to the feeding tube 140 in a variety of configurations, the preferred embodiment uses a configuration similar to that of the balloon catheter construction disclosed by U.S. Pat. No. 5,522,961, which is incorporated by reference herewith. This preferred configuration defines an energy-absorbing end to reduce the risk of trauma to the patient during placement of the feeding tube 140. Preferably, however, and unlike the disclosure of U.S. Pat. No. 5,522,961, the balloon-type retaining member for the feeding tube 140 is attached using a conventional heat fusion technique. Solvents and epoxy materials are not required. In the preferred embodiment, the balloon member itself has a nominal thickness of about 0.002 inches, and is made of Estane 58309 available from BF Goodrich, or an equivalent material thereof.

If a balloon-type retaining member is provided, it is preferred that the feeding tube 140 define at least two lumen therethrough; one lumen defining a feeding lumen 143 for the introduction of enteral nutritional products and the like, and another lumen defining a filling lumen 145 for inflation and deflation of the retaining member 146, as shown in FIG. 7. The feeding lumen 143 therefore extends through the length of the feeding tube 140, while the filling lumen 145 extends at least from the first end portion 141 of the feeding tube 140 to an access opening into the internal chamber of the balloon-type retaining member 146. FIG. 7 shows the feeding lumen 143 having a substantially D-shaped cross-section, with the filling lumen 145 disposed proximal the flat interior edge of feeding lumen 143. In this embodiment, filling lumen 145 can have either a circular or elliptical cross-section, and preferably the feeding tube 140 has a generally circular external cross-sectional configuration. Alternative multi-lumen feeding tube configurations and constructions also can be used.

Although not necessary, it is preferred that the feeding tube assembly 100 of the present invention also include a radiopaque rod 170 or member provided to assist in proper placement of the feeding tube 140 using X-ray or similar imaging techniques. For example, and as embodied herein, the filling lumen 145 can extend entirely from the first end portion 141 to the second end portion 142 of the feeding tube 140. A rod 170 of known radiopaque material thus can be inserted into the filling lumen 145 at the second end portion of the feeding tube 140 so as to extend up to the access opening of the retaining member 140. Alternatively, the feeding tube itself can be made of a known radiopaque material or be formed with a stripe of radiopaque material extending all or a portion of the length thereof.

Secondary placement of the feeding tube assembly 100 of the present invention can be performed in a conventional manner. For example, if nasoenteric access is desired, the feeding tube assembly 100 may or may not be provided with a retaining member, as well as a weighted tip (not shown) at the second end portion 142 of the feeding tube 140 as is well known. The second end portion 142 is thus inserted into the patient's nostril and guided to the desired position in the gastrointestinal tract. The balloon-type retaining member, if provided, is then inflated to secure placement of the feeding tube.

If secondary placement through a mature stoma is desired, retaining members are provided as previously described. When a balloon-type retaining member is used, for example, the retaining member 146 is deflated for initial insertion of the second end portion 142 of the feeding tube 140 into the stoma. Once properly positioned, the retaining member 146 is filled with an appropriate fluid via the appropriate inlet conduit 157 and filling lumen 145 to expand the retaining member 146 and engage an inner wall of the patient proximate the stoma. The feeding tube 140 of the present invention also can include an external retaining disc, also known as a skin disk 172, as described above. The skin disk 172 is mounted for movement along the feeding tube 140, so as to be positioned against the patient's exterior abdominal wall to secure the placement of the feeding tube assembly 100. The removable cap 160 thus can be selectively removed, with limited risk of self adhesion or bonding to the inlet conduit 156, to allow enteral nutritional feeding or the like.

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents.

What is claimed is:

1. A feeding tube assembly comprising:
    a feeding tube adaptor made of polyurethane, the feeding tube adaptor including an elongated first inlet conduit having an inlet port, the feeding tube adaptor also including an outlet conduit for fluid communication with an inlet conduit of a feeding tube; and
    a cap made of polyurethane removably attached to close selectively the inlet port of the first inlet conduit, the cap having a surface with a surface configuration such that a portion of the surface engages a portion of a corresponding surface of the first inlet conduit, the surface configuration of the cap being noncomplementary to a corresponding surface configuration of the first inlet conduit in a common transverse plane such that the cap frictionally closes the inlet port of the first inlet conduit, wherein the surface configuration of the cap defines a cross-sectional shape different than that of the corresponding surface configuration of the first inlet conduit in the common transverse plane.

2. A feeding tube assembly according to claim 1, wherein the cap is permanently connected to the feeding tube adaptor by a tether member.

3. A feeding tube assembly according to claim 1, wherein the port of the first inlet conduit is defined by an interior surface and the cap includes a plug to be inserted into the port, the engaging surface of the cap being an exterior surface of the plug and the corresponding surface being the interior surface of the inlet conduit.

4. A feeding tube assembly according to claim 1, wherein the cap includes a peripheral flange, the engaging surface of the cap being an interior surface of the peripheral flange and the corresponding surface being an exterior surface of the first inlet conduit.

5. A feeding tube assembly according to claim 1, wherein at least one of the engagement surface and the corresponding surface is provided with a series of longitudinal protuberances.

6. A feeding tube assembly according to claim 1, wherein at least one of the engagement surface and the corresponding surface is provided with a series of longitudinal indents.

7. A feeding tube assembly according to claim 1, further comprising a feeding tube having a first end portion, a second end portion opposite the first end portion, and at least one lumen defined therein extending between the first end portion and the second end portion; the outlet conduit of the feeding tube adaptor connected in fluid communication with the first end portion of the feeding tube.

8. A feeding tube assembly according to claim 7, wherein the feeding tube is made of a Carbothane material.

9. A feeding tube assembly according to claim 7, further comprising a retaining member attached to the second end portion of the feeding tube.

10. A feeding tube assembly according to claim 9, wherein the retaining member is made of an Estane material.

* * * * *